United States Patent
Anderson et al.

(10) Patent No.: US 6,436,124 B1
(45) Date of Patent: Aug. 20, 2002

(54) SUTURE ANCHOR

(75) Inventors: David W. Anderson, Bryn Mawr, PA (US); Pertti Helevirta, Tampere (FI); Eija Pirhonen, Tampere (FI); Timo Pohjonen, Tampere (FI); Markku Tamminmäki, Tampere (FI); Pertti Törmälä, Tampere (FI)

(73) Assignee: Bionx Implants Oy, Tampere (FI)

( * ) Notice: Subject to any disclaimer, the term of this patent is extended or adjusted under 35 U.S.C. 154(b) by 0 days.

(21) Appl. No.: 09/331,485

(22) PCT Filed: Dec. 3, 1997

(86) PCT No.: PCT/US97/22428

§ 371 (c)(1),
(2), (4) Date: Nov. 16, 1999

(87) PCT Pub. No.: WO98/26717

PCT Pub. Date: Jun. 25, 1998

(30) Foreign Application Priority Data

Dec. 19, 1996 (FI) .................................................. 965111

(51) Int. Cl.[7] .............................................. A61B 17/60
(52) U.S. Cl. ........................................ 606/232; 606/72
(58) Field of Search ................................ 606/232–233, 606/72–75; 433/173; 411/418, 422

(56) References Cited

U.S. PATENT DOCUMENTS

| | | | |
|---|---|---|---|
| 5,037,422 A | | 8/1991 | Hayhurst et al. ............. 606/72 |
| 5,156,616 A | | 10/1992 | Meadows et al. ........... 606/232 |
| 5,176,682 A | * | 1/1993 | Chow ........................ 606/232 |
| 5,258,016 A | * | 11/1993 | DiPoto et al. .............. 606/232 |
| 5,472,452 A | | 12/1995 | Trott ......................... 606/232 |
| 5,527,342 A | * | 6/1996 | Pietrzak et al. ............. 606/232 |
| 5,573,548 A | * | 11/1996 | Nazre et al. ................ 606/232 |
| 5,584,695 A | * | 12/1996 | Lal Sachdeva et al. ..... 433/173 |
| 5,593,425 A | * | 1/1997 | Bonutti et al. .............. 606/232 |
| 5,601,557 A | * | 2/1997 | Hayhurst .................... 606/72 |

FOREIGN PATENT DOCUMENTS

WO    WO 9314705 A    8/1993

* cited by examiner

*Primary Examiner*—Cary E. O'Connor
(74) *Attorney, Agent, or Firm*—Kenyon & Kenyon

(57) ABSTRACT

A one-piece suture anchor for anchoring a suture into a bone comprising an elongated body having proximal and distal ends, the body comprising at least one channel for receiving a suture, the channel comprising two elongated longitudinal guides continuing from the proximal end of the suture anchor towards the distal end of the anchor suture, wherein the guides are connected to each other by a section of channel that is configured such that it is not bent at any given point at an angle greater than or equal to ninety degrees.

10 Claims, 9 Drawing Sheets

SUTURE ANCHOR

FIELD OF THE INVENTION

The present invention relates to a suture anchor for attaching suture to body tissue, such as bone.

BACKGROUND OF THE INVENTION

Suture anchors are used in surgery, in particular in orthopedic surgical operations for placing a part of the suture in and attaching it to a bone, wherein the part of the suture that is not attached, most commonly two parts projecting from the bone, can be further used e.g. for connecting detached connective tissue, such as ligament, to the bone. To place the suture anchor into a bone, a hole is made in the bone, e.g. by drilling, into which hole the suture anchor and a part of the suture is inserted, wherein the object of the suture anchor is to keep the suture firmly in the bone, in particular during and after the orthopedic operation.

In respect of the prevailing level of technology in the field, reference is made mainly to the following patents: U.S. Pat. No. 5,156,616, U.S. Pat. No. 5,472,452 and U.S. Pat. No. 5,037,422.

In accordance with the suture anchor of patent U.S. Pat. No. 5,156,616, two separate sutures are inserted through a hole penetrating the body of the suture anchor in the longitudinal direction and situated substantially in the middle of the cross-section of the anchor body in a manner that the other ends of the sutures extend clearly outside the end at the base side of the suture anchor and the ends at the head side of the suture anchor are tied together, wherein the knot formed thereby prevents the suture from gliding through the hole, out from the suture anchor via its base. The suture anchor is provided with screw threads.

The suture anchor in accordance with patent U.S. Pat. No. 5,472,452 comprises a tubular body having a substantially quadrangular cross-sectional form, and a core part to be inserted therein. Two walls of the anchor body are provided with projecting branches which are pressed by the core part against the walls of a hole formed in the bone when the suture anchor is pressed into the hole. The branches are further provided with means which can be grabbed by a special tool, e.g. for moving the suture anchor inside the hole. The suture is arranged to circle outside the anchor body via two of its opposite vertical walls and heads. For implementation of this, the heads of said two vertical walls are provided with cuttings in which the suture is placed at the head of the anchor body.

The suture anchor of patent U.S. Pat. No. 5,037,422 is composed of a conical, hollow body which is positioned by pressing or hitting in a hole made in the bone. For keeping the anchor body in its place, it is provided with two splits situated substantially at the opposite walls thereof and having a cross-section parallel with the suture anchor, wherein the anchor body is contracted when inserted in the hole, tending to expand by pressing the gearing that is formed on the outer surface of the anchor body against the walls of the hole. The suture is positioned to travel substantially through the splits, parallel with them, and arranged to circle via a substantially straight, tubular turning portion situated in the vicinity of the head of the anchor body.

The suture anchor in accordance with the prior-mentioned patent U.S. Pat. No. 5,156,616 has a simple structure and comprises a screw-thread arrangement which is advantageous when placed in a bone. However, it is unsafe to keep the sutures tied in the suture anchor merely supported by said knot, and it is not possible to fully prevent the sutures from being damaged, in particular at the junction of the knot and the hole penetrating the suture anchor. Furthermore, a device installed in the base of the suture anchor for threading the suture anchor into the bone can damage the sutures, which are situated partially in a sleeve formed for the head of said device in the base of the anchor body.

The drawbacks of the two other solutions mentioned above (U.S. Pat. No. 5,472,452 and U.S. Pat. No. 5,037,422) are mainly related to the complexity in their structure and use. A particular drawback is that the suture channels through which the sutures are intended to be placed in the suture anchor are formed in a manner that harmfully abrupt alterations of direction take place, in particular adjacent to the heads of the suture anchors (an abrupt alteration of direction of about 90°) which easily results in partial breaking or even cutting off of the suture when the suture is tightened in a later phase of the orthopedic surgical procedure, because the suture is subjected to a strong tensile stress on its outermost surface.

The object of the invention is to introduce a suture anchor whereby the above-described shortcomings pertaining to known suture anchors can be eliminated to a great extent and thus the prevailing level of technology in the field can be elevated.

SUMMARY OF THE INVENTION

For achieving this object, the suture anchor according to the invention is characterized by a novel arrangement between the body of the suture anchor and the suture. This novel arrangement prevents the formation of abrupt alterations of course which add to the risk of damaging the suture. The body of the suture anchor consists of a single part, and the suture channel in which the suture is placed is entirely formed in the anchor body without any separate means and is composed of two longitudinal guides and a particularly curved turning portion which connects them. By means of this arrangement, in particular in view of the turning portion, the tensile strength of the suture required in the surgical operation can be maximally utilized. The primary characteristics of the suture anchor of the invention will be presented in the characterizing portion of the appended Claim 1.

The simple, substantially closed structure of the anchor body markedly adds to the strength of the suture anchor and thus also increases its operational reliability. The arrangements related to the suture channel also efficiently prevent the risk of damaging, which is present when bringing the suture anchor in the bone and which is particularly caused when the suture gets in contact with the surface of the bone of the drill canal.

The above-mentioned features and other features characteristic to the present invention, as well as embodiments of the invention will be presented in the accompanying dependent Claims.

BRIEF DESCRIPTION OF THE DRAWINGS

The invention will be illustrated in more detail in the following specification, with reference made to the accompanying drawings. In the drawings.

DETAILED DESCRIPTION OF PREFERRED EMBODIMENTS OF THE INVENTION

Figure 1:
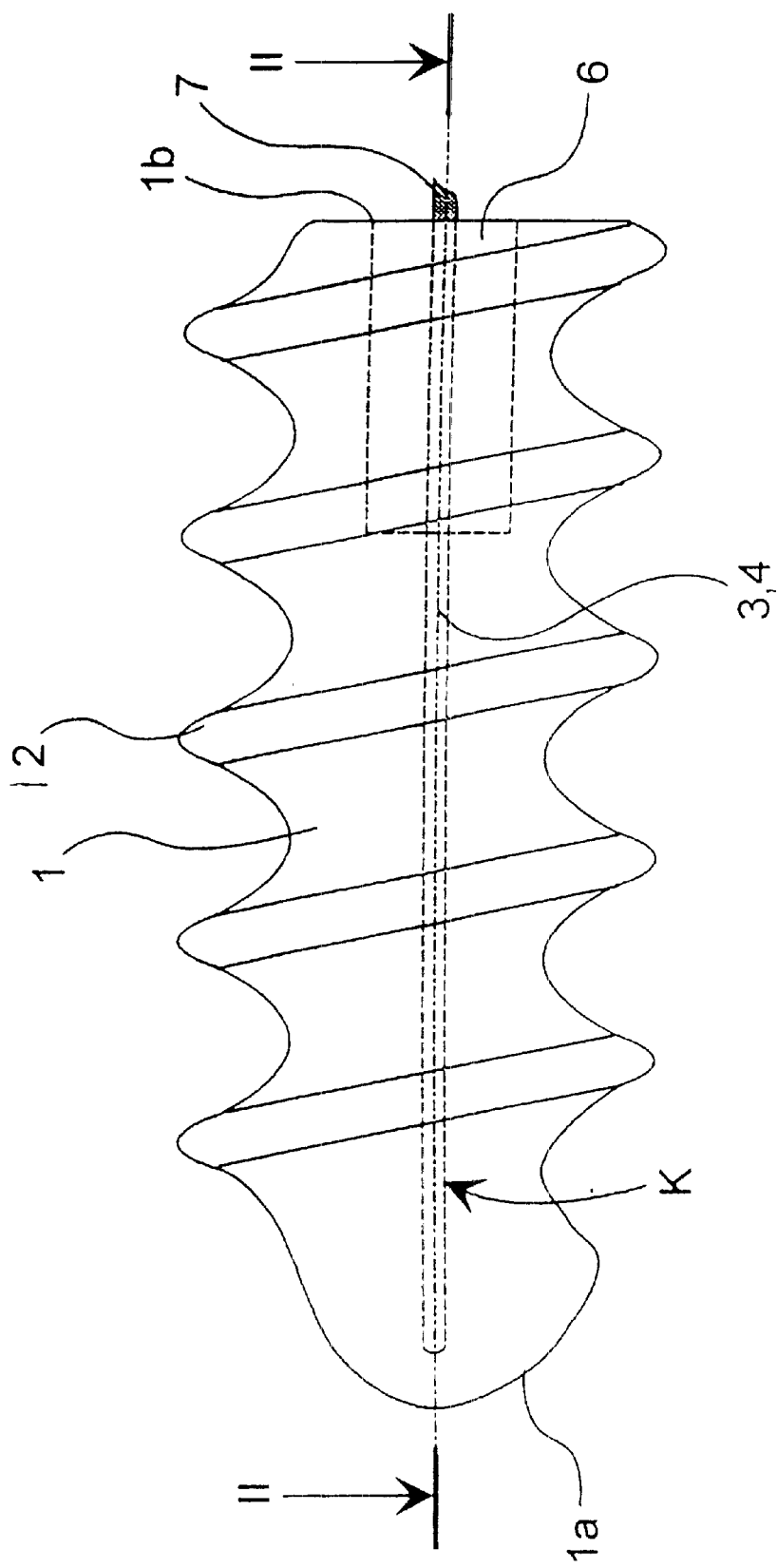
FIGS. 1 to 8 show various embodiments of the suture anchor as seen from the side (FIGS. 1, 3, 5 and 7) and corresponding cross-sections in the direction of the longitudinal axis at the location of the suture channel (FIGS. 2, 4, 6 and 8)

The suture anchor of the present invention comprises a substantially closed and elongated body 1 which is preferably manufactured of a single piece and has preferably a circular cross-section. The longitudinal outer surface of the anchor body 1 is advantageously provided with a set of projections, advantageously a screw thread 2 having the same size as the longitudinal side of the anchor body 1, for placing the suture anchor, in particular by threading, in a hole formed in the bone. The set of projections can optionally have e.g. a scale-like structure. In this respect reference is made to the structure described in patent Fl-95537.

The anchor body 1 is preferably manufactured of some bioabsorbable material, wherein it is usually not necessary to remove it from the bone, but is it obvious that the possible removal and/or precise moving of a suture anchor provided with a screw thread 2 can be carried out in the drill canal or hole formed in the bone in a fairly easy manner. It is self-evident that the screw thread 2 does not require the suture anchor to be positioned in the bone by threading; instead it is possible to insert it into the hole e.g. simply by pressing or hitting.

The head of the anchor body 1a is preferably formed in a manner that it tapers at least to some extent towards the peak of the head. It is also advantageous that the head of the anchor body 1 is rounded. In the base 1b of the anchor body, connecting means 6 are formed for connecting an external device with the anchor body for placing the suture anchor in the bone, wherein the connecting means can comprise e.g. a sleeve wrench or the like for the blade part.

The suture channel K for binding the suture 7 to the suture anchor is entirely formed in the anchor body 1 by using grooves, tubular holes and/or combinations thereof in order to constitute substantially U-formed arrangements. Thus, for example owing to details pertaining to manufacturing techniques and/or bringing the suture anchor in operatable condition, the suture channel K can be formed in accordance with the embodiments shown in the drawings.

The suture channel K comprises two longitudinal guides 3, 4 and a turning portion 5 connecting them at their ends of the head 1a side of the suture anchor. The longitudinal guides 3, 4 are situated in the anchor body 1 substantially in accordance with the longitudinal direction thereof and, also, substantially on the opposite directions of the longitudinal central line of the anchor body 1. The turning portion 5 is situated at the end of the head 1a side of the longitudinal guides 3, 4 and constituting an extension thereto. It is characteristic to the invention that the turning portion 5 is preferably a continuous curved form, e.g. a circle form, wherein in the area of the suture channel K, no abrupt, sharp angles or the like are formed in the suture 7 placed in the suture channel K, at which the risk of damaging the suture would be particularly notable in situations in which the suture is subjected to a power influence, said power influence tightening the suture especially during or after a surgical operation. The effect of the form of the turning point 5 on tensile strength is illustrated at the end of the specification by means of an example describing one experimental arrangement.

Since the duration of the tensile stress on the suture can be influenced expressly by the design of the turning portion 5, in particular with the grade of curvature, it is substantial that the turning portion 5 is formed in a manner that the bending radius of the suture 7 placed therein does not cause substantial tensile stress on the outermost surface of the suture 7 when the suture is subjected to an effective force parallel with the longitudinal guides 3, 4 and directed towards the base 1b of the anchor body 1 in connection with a surgical operation. To implement this object, all the embodiments that will be described in the following share the common feature that the turning portion 5 extends in the longitudinal alignment of the suture anchor, wherein a turning point KP at the top of the turning portion 5 is located at a distance L from the junctions 5a, 5b of the longitudinal guides 3, 4 and the turning portion 5.

This results in the fact that every alteration angle at the turning portion is smaller than 90° or, in particular (as in the advantageous embodiments shown in the Figures) that the alteration angle of the turning portion 5 is continuous and the turning portion 5 has a curved configuration.

Figure 2:
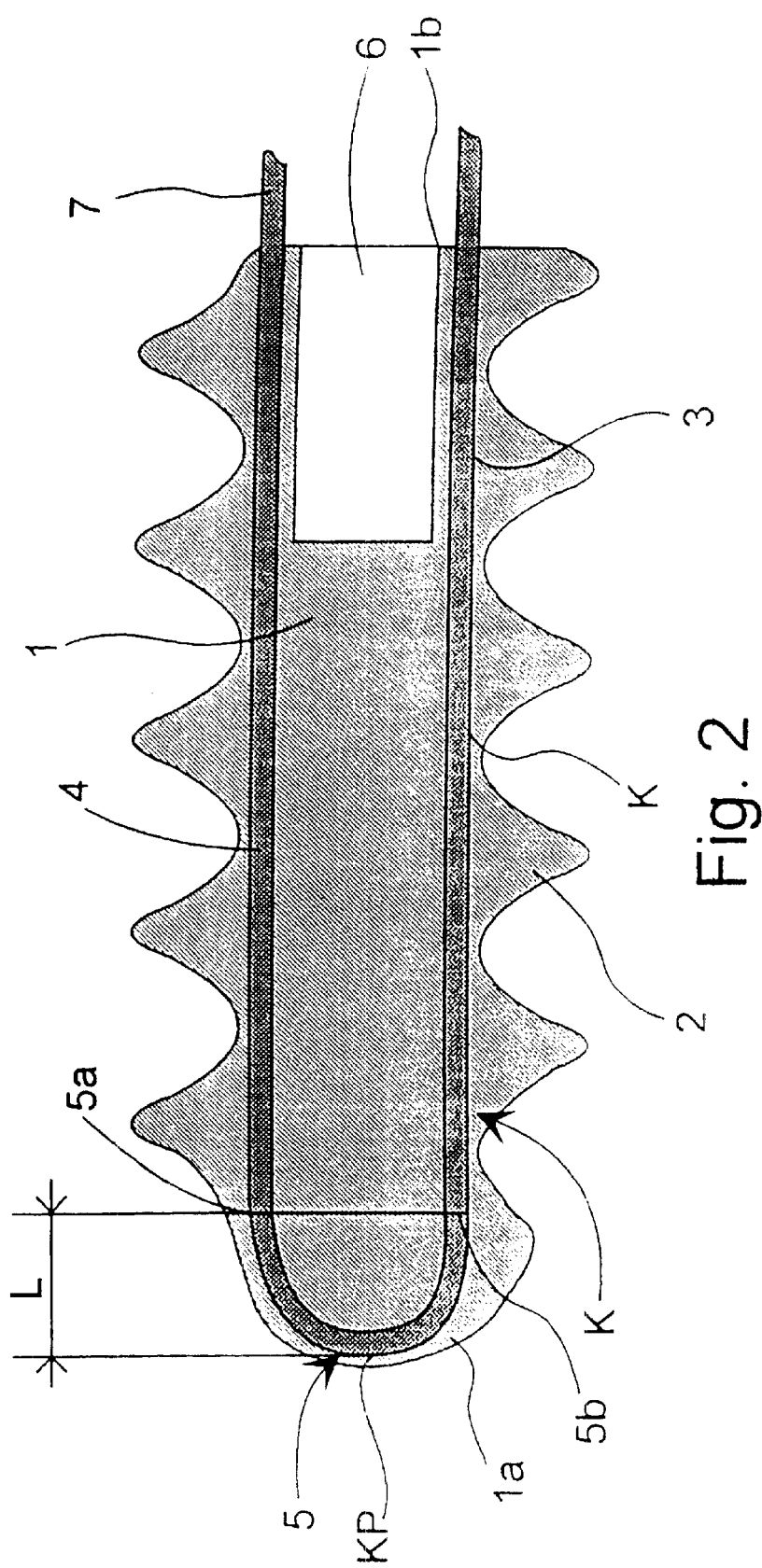

FIGS. 1 and 2 show an embodiment of the suture anchor, wherein the suture channel K is formed entirely inside the anchor body 1, wherein the longitudinal guides 3, 4 are holes that are open at the base 1b of the anchor body 5, directed towards the top 1a of the anchor body, and situated substantially in alignment, preferably on the opposite sides of the longitudinal central line of the anchor body 1, adjacent to the outer surface of the anchor body 1, at the base parts of the screw thread 2. A curved, preferably circular hole forming the turning portion 5 and placed entirely inside the anchor body 1 is situated successive to the longitudinal guides 3, 4 combining their head 1a ends at the junctions 5a, 5b.

Figure 3:
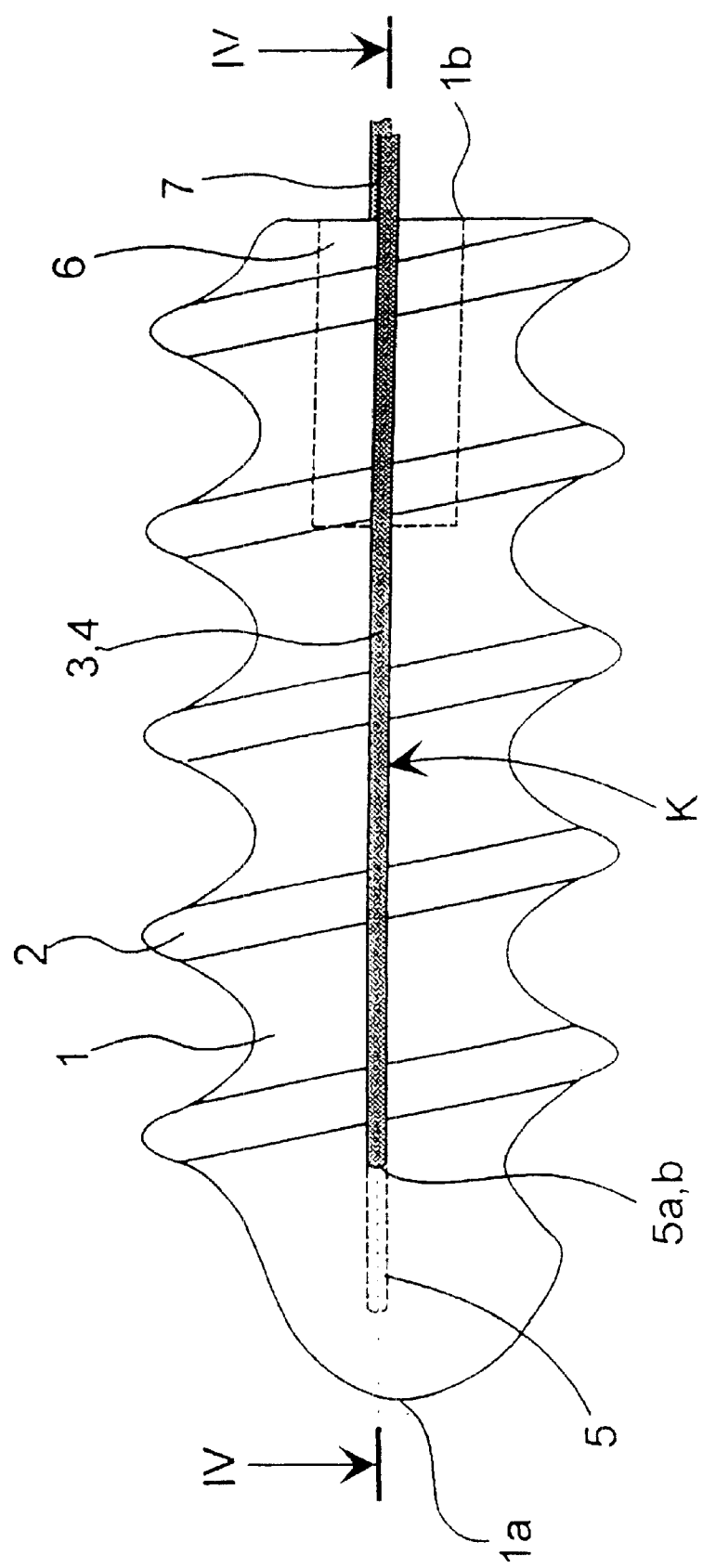
Figure 4:
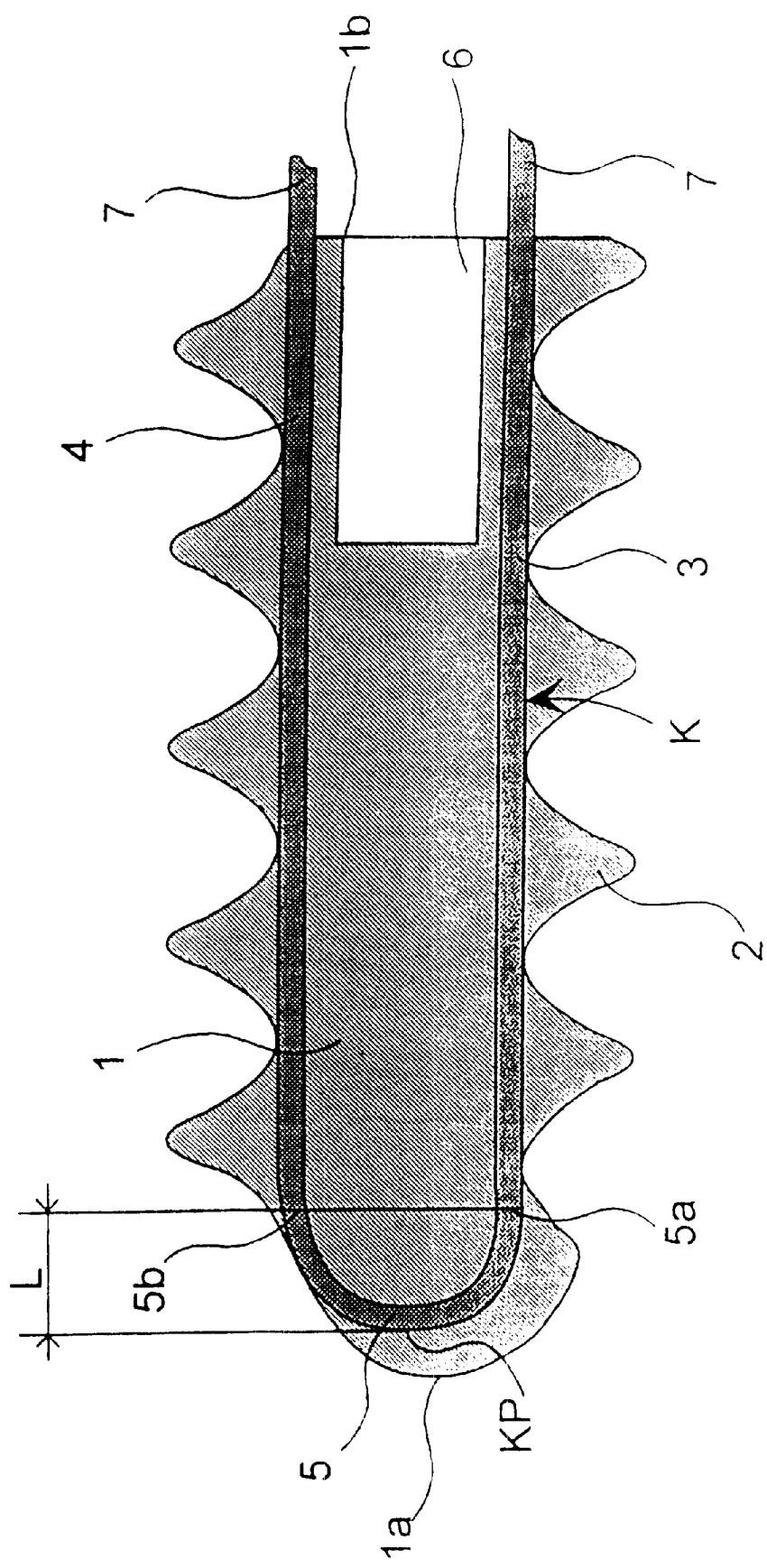

FIGS. 3 and 4 show a suture anchor having longitudinal guides 3, 4 of then suture channel K which consist of two grooves made in the outer surface of the anchor body 3, said grooves being situated preferably at the opposite sides of the anchor body 1 and extending from the base 1b of the anchor body to the ends of the curved, preferably circular hole situated inside the anchor body 1 and forming the turning portion 5, wherein the junctions 5a, 5b that are situated on the outer surface of the anchor body 1 are constituted.

Figure 5:
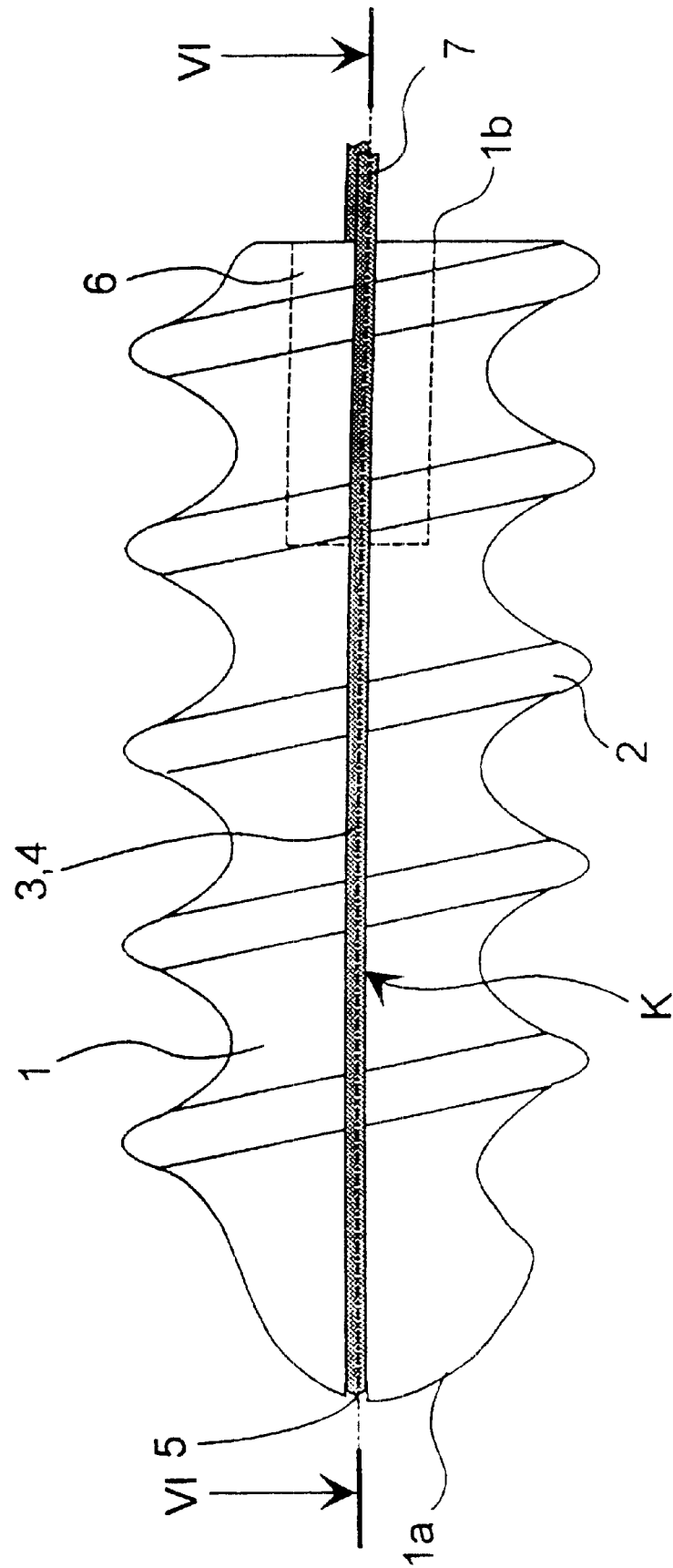
Figure 6:
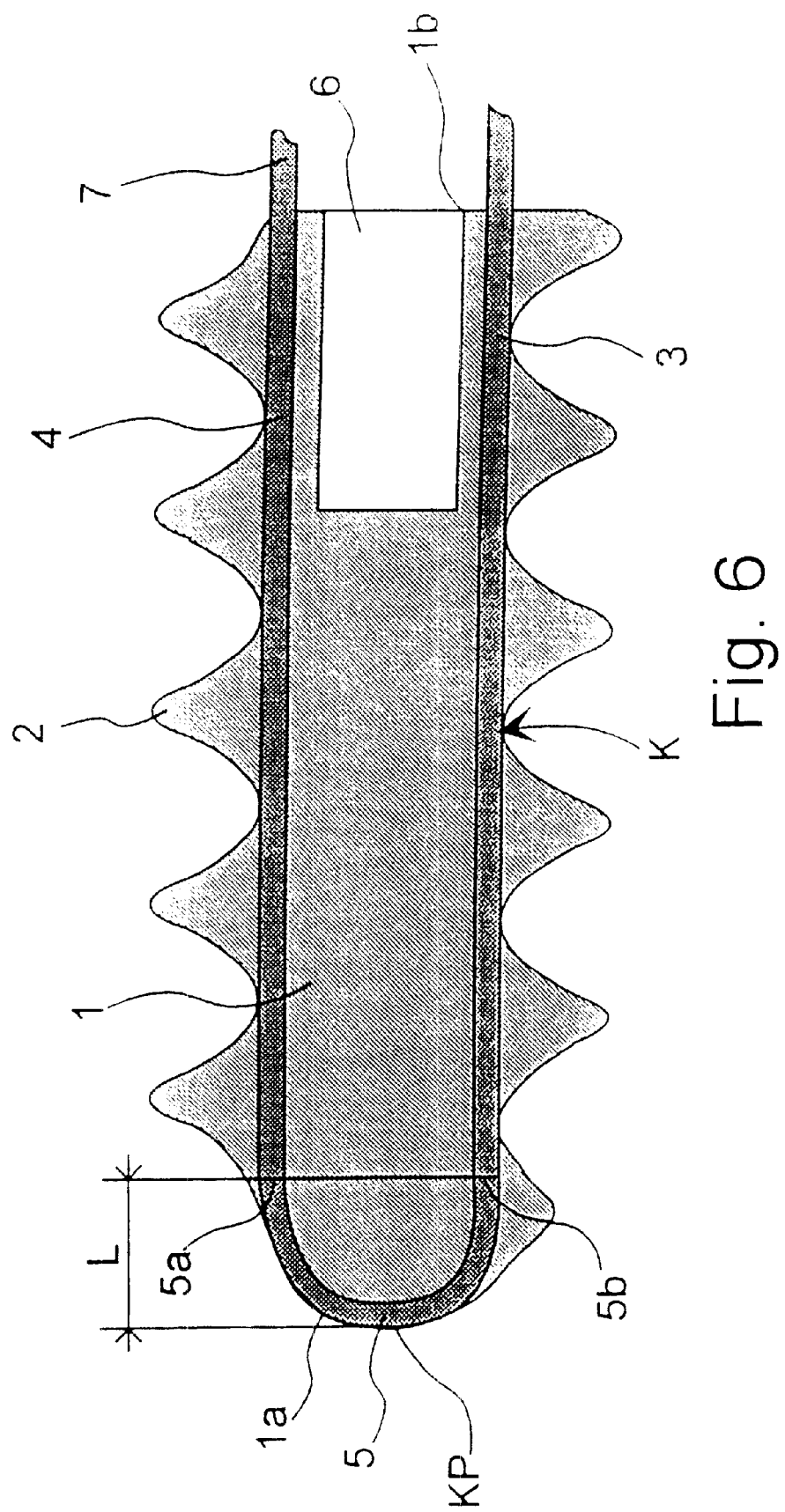

FIGS. 5 and 6 illustrate an embodiment where both the longitudinal guides 3, 4 of the suture channel K and the turning portion 5 have a groove form and are situated on the surface of the anchor body 1, wherein the turning portion 5 is formed at the head 1a of the anchor body 3, on the outer surface thereof, to pass the head 1a in curved, preferably circular groove form, wherein the longitudinal guides 3, 4 connected to the ends of the groove-formed turning portion 5 at the junctions 5a, 5b are placed on the opposite sides of the anchor body 1, substantially parallel with the longitudinal direction of the anchor body 1, to extend to the base 1b of the anchor body.

Figure 7:
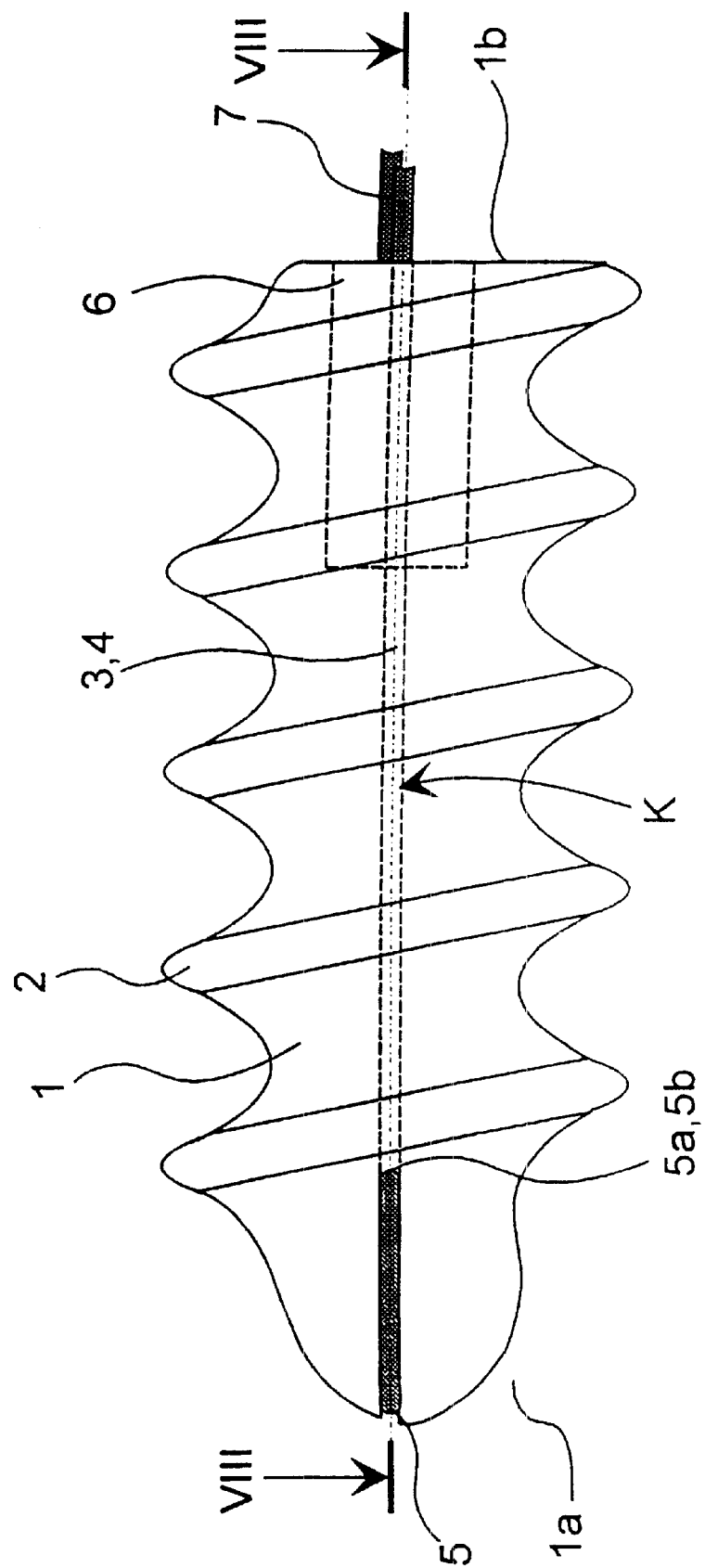
Figure 8:
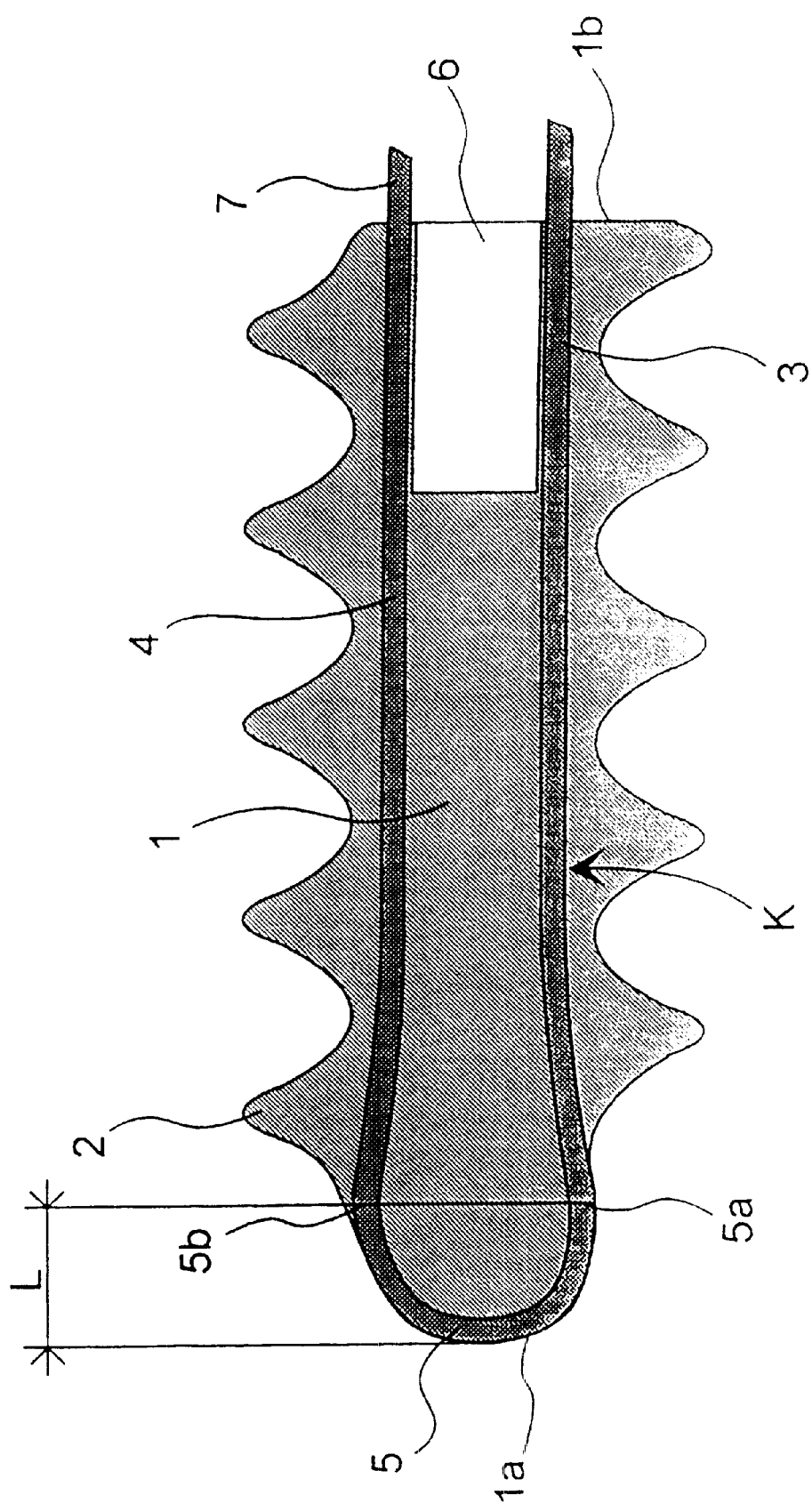
Figure 9:
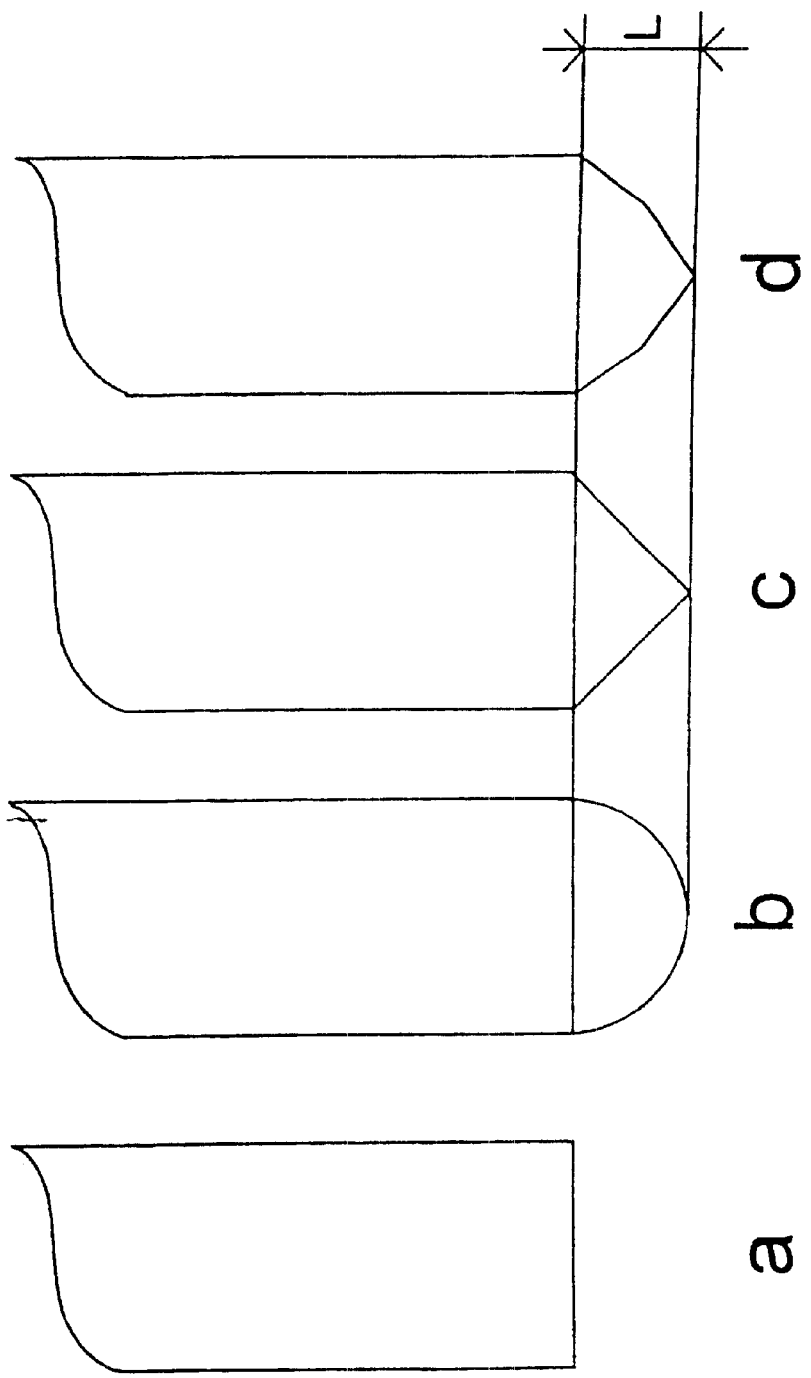
FIGS. 9a to d show heads of various suture anchors used in the test arrangement illustrated as an example.

As shown in FIGS. 7 and 8, the turning portion 5 of the suture channel K constitutes a groove at the head 1a of the anchor body 1, in a respective manner as in the embodiment of FIG. 3, but the longitudinal guides 3, 4 are formed inside the anchor body 1 (cf. FIG. 1) in a manner that they constitute holes which penetrate the anchor body 1 in its longitudinal direction and extend from the base 1b to the ends of the turning portion 5, up to the junctions 5a, 5b.

It is obvious that the longitudinal guides 3, 4 can easily be placed in the base 1b area so that the connecting means 6 can be formed between the longitudinal guides 3, 4 and the connecting means 6 can be used without causing any risk of damaging the suture 7 itself, e.g. when the suture anchor is seated into the bone.

The functionality of the invention is illustrated in the following example.

Four suture anchors (FIG. 9a to d) of various types, in particular with a regard to the form of the turning portion 5, were manufactured, wherein the head form *a* is a so-called blunt head, wherein the suture has to circle the head substantially via two abrupt angles of about 90° (cf. U.S. Pat. No. 5,472,452 and U.S. Pat. No. 5,524,946), the head form *b* is one advantageous head form in accordance with the invention, this head form being a curved, preferably a circled form, the head form *c* is included within the scope of the inventive idea, being a pointed form, in which the suture has to circle via three alterations of course (angles e.g. 60 °), and the head form *d* comprises more than three angles, e.g. five angles of 36°.

The aim of the test was to demonstrate how the form of the head of the suture anchor affects the suture Dexon® (USP 1) placed in the suture anchor. The suture anchors were attached to first jaws of a device for measuring tensile strength, and the free ends of the suture were attached to second jaws of the device, whereafter the suture was subjected to an effective force, said effective force stretching the suture for breaking it off. In the test, the following minimum effective forces were obtained for breaking off the suture:

a) 87 to 96 N b) 186 to 210 N c) 153 to 161 N d) 154 to 187 N

The results indicate that the turning portion form *b*, which, in accordance with the invention, is the most advantageous form for the turning point in the suture anchor, gives the best results in view of the tensile strength. The options *c* and *d* improve the tensile strength substantially compared to the option *a*.

The invention is neither limited solely to what is described above nor to the embodiments illustrated in the Figures, but it can be modified within the scope of the inventive idea presented in the accompanying Claims.

What is claimed is:

1. A one-piece suture anchor for anchoring a suture into a bone comprising an elongated body having proximal and distal ends, said body comprising at least one channel for receiving a suture, said channel comprising two elongated longitudinal guides continuing from said proximal end of said suture anchor towards said distal end of said suture anchor, wherein said guides are connected to each other by a section of said channel that is not bent at any given point at an angle greater than or equal to ninety degrees and wherein said channel is contained within said body of said suture anchor, and further wherein said proximal end of said suture anchor has connecting means capable of connecting said suture anchor to a delivery device.

2. The suture anchor as claimed in claim 1, wherein said section of said channel connecting said guides is a continuous curve.

3. The suture anchor as claimed in claim 1, wherein said longitudinal guides and said section of said channel that connects said longitudinal guides comprise tunnels contained within said body of said suture anchor.

4. The suture anchor as claimed in claim 1, wherein said longitudinal guides comprise a groove formed on the surface of said suture anchor.

5. The suture anchor as claimed in claim 1, wherein said section of said channel that connects said longitudinal guides comprises a groove formed on the surface of said distal end of said suture anchor.

6. The suture anchor as claimed in claim 1, wherein said longitudinal guides and said section of said channel that connects said longitudinal guides comprise a grove formed on the surface of said suture anchor.

7. The suture anchor as claimed in claim 1, wherein said surface of said suture anchor comprise s a plurality of projections.

8. The suture anchor as claimed in claim 7, wherein said projections comprise screw thread.

9. The suture anchor as claimed in claim 1, wherein said proximal end of said suture anchor comprises an indentation for receiving a device for inserting said suture anchor.

10. The suture anchor as claimed in claim 1 wherein said suture anchor is biodegradable.

* * * * *

UNITED STATES PATENT AND TRADEMARK OFFICE
CERTIFICATE OF CORRECTION

PATENT NO. : 6,436,124 B2
DATED : August 20, 2002
INVENTOR(S) : Anderson et al.

It is certified that error appears in the above-identified patent and that said Letters Patent is hereby corrected as shown below:

Title page,
Item [57], ABSTRACT,
Lines 2 and 3, after "ends", and before "body comprising" change "the" to -- said --;
Line 4, after "suture", and before "channel comprising" change "the" to -- said --;
Line 5, after "from", and before "proximal end" change "the" to -- said --;
Line 6, after "of", and before "anchor, suture" change "the" to -- said --;
Line 7, after "wherein", and before "guides" change "the" to -- said --;

Column 6,
Line 31, change "grove" to -- groove --;
Line 34, change "comprise s" to -- comprises --.

Signed and Sealed this

Twelfth Day of August, 2003

JAMES E. ROGAN
*Director of the United States Patent and Trademark Office*